US010189791B2

(12) United States Patent
Sporn et al.

(10) Patent No.: US 10,189,791 B2
(45) Date of Patent: Jan. 29, 2019

(54) PYRIDYL ANALOGS OF 1-(2-CYANO-3,12-DIOXOOLEANA-1,9(11) DIEN-28-OYL) IMIDAZOLE

(71) Applicant: Trustees of Dartmouth College, Hanover, NH (US)

(72) Inventors: Michael B. Sporn, Tunbridge, VT (US); Gordon W. Gribble, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 15/861,972

(22) Filed: Jan. 4, 2018

(65) Prior Publication Data

US 2018/0127379 A1 May 10, 2018

Related U.S. Application Data

(63) Continuation-in-part of application No. 15/505,327, filed as application No. PCT/US2015/046845 on Aug. 26, 2015, now Pat. No. 9,896,475.

(60) Provisional application No. 62/041,802, filed on Aug. 26, 2014.

(51) Int. Cl.
C07D 233/60 (2006.01)
C07D 401/04 (2006.01)
A61K 31/4164 (2006.01)

(52) U.S. Cl.
CPC ........ C07D 233/60 (2013.01); A61K 31/4164 (2013.01); C07D 401/04 (2013.01)

(58) Field of Classification Search
CPC .......................... C07D 233/60; A61K 31/4178
See application file for complete search history.

(56) References Cited

U.S. PATENT DOCUMENTS

| | | | |
|---|---|---|---|
| 6,326,507 B1 | 12/2001 | Gribble et al. | 558/415 |
| 6,552,075 B2 | 4/2003 | Gribble et al. | 514/522 |
| 6,974,801 B2 | 12/2005 | Honda et al. | 514/25 |
| 7,288,568 B2 | 10/2007 | Gribble et al. | 514/519 |
| 7,435,755 B2 | 10/2008 | Konopleva et al. | 514/510 |
| 7,795,305 B2 | 9/2010 | Konopleva et al. | 514/510 |
| 7,863,327 B2 | 1/2011 | Gribble et al. | 514/521 |
| 7,915,402 B2 | 3/2011 | Anderson et al. | 540/519 |
| 7,943,778 B2 | 5/2011 | Jiang et al. | 548/247 |
| 8,034,955 B2 | 10/2011 | Gribble et al. | 548/241 |
| 9,896,475 B2 | 2/2018 | Gribble et al. | C07J 61/00 |
| 2004/0002463 A1 | 1/2004 | Honda et al. | 514/25 |
| 2008/0233195 A1 | 9/2008 | Sporn et al. | 424/486 |
| 2009/0018146 A1 | 1/2009 | Gutterman et al. | 514/255.06 |
| 2009/0048204 A1 | 2/2009 | Walling et al. | 514/49 |
| 2009/0048205 A1 | 2/2009 | Meyer et al. | 514/49 |
| 2009/0060873 A1 | 3/2009 | Sporn et al. | 424/85.6 |
| 2009/0326063 A1 | 12/2009 | Sporn et al. | 514/529 |
| 2010/0048887 A1 | 2/2010 | Anderson et al. | 540/8 |
| 2010/0048892 A1 | 2/2010 | Anderson et al. | 544/154 |
| 2010/0048911 A1 | 2/2010 | Jiang et al. | 548/250 |
| 2011/0245206 A1 | 10/2011 | Jiang et al. | 514/112 |
| 2011/0245233 A1 | 10/2011 | Anderson et al. | 514/212.04 |
| 2013/0303607 A1 | 11/2013 | Gribble et al. | 514/510 |
| 2013/0303797 A1 | 11/2013 | Gribble et al. | 558/337 |

FOREIGN PATENT DOCUMENTS

| | | |
|---|---|---|
| WO | WO2002/047611 | 6/2002 |
| WO | WO2004/064723 | 8/2004 |
| WO | WO2005/046732 | 5/2005 |
| WO | WO2008/064132 | 5/2008 |
| WO | WO2008/136838 | 11/2008 |
| WO | WO2009/023232 | 2/2009 |
| WO | WO2009/023845 | 2/2009 |
| WO | WO2012/093944 | 8/2010 |
| WO | WO2016033132 | * 3/2016 |

OTHER PUBLICATIONS

Isomer, retrieved from https://biologydictionary.net/isomer/ on Apr. 23, 2018 (Year: 2018).*
Cao, Pharmacological Research, 2015, vol. 100, p. 135-147. (Year: 2015).*
Honda, et al. "New enone derivatives of oleanolic acid and ursolic acid as inhibitore of nitric oxide production in mouse macrophages" (1997) Bioorg. Med. Chem. Lett. 7:1623-1628.
Honda, et al. "Design and Synthesis of 2-Cyano-3,12-Dioxoolean-1,9-Dien-28-Oic Acid, a Novel and Highly Active Inhibitor of Nitric Oxide Production in Mouse Macrophages" (1998) Bioorg Med Chem Lett. 8(19):2711-2714.
Huang, et al. "Inhibition of Skin Tumorigenesis by Rosemary and Its Constituents Carnosol and Ursolic Acid" (1994) Cancer Res. 54:701-708.
Moncada, et al. "Nitric oxide: physiology, pathophysiology, and pharmacology." (1991) Pharmacol. Rev. 43:109-142.
Nathan & Xie "Nitric oxide synthases: roles, tolls and controls" (1994) Cell 78:915-918.
Nishino, et al. "Inhibition of the tumor-promoting action of 12-O-tetradecanoylphorbol-13-accetate by some oleanane-type triterpenoid compounds" (1988) Cancer Res. 48:5210-5215.
Ohshima & Bartsch "Chronic infections and inflammatory processes as cancer risk factors: possible role of nitric oxide in carcinogenesis." (1994) Mutat. Res. 305:253-264.
Siebert & Masferrer "Role of inducible cyclooxygenase (COX-2) in inflammation." (1994) Receptor 4(1):17-23.
Sporn & Roberts "Peptide growth factors and inflammation, tissue repair, and cancer" (1986) J. Clin. Invest. 78:329-332.
Tamir & Tannebaum "The role of nitric oxide (NO.) in the carcinogenic process." (1996) Biochim. Biophys. Acta 1288:F31-F36.
International Search Report and Written Opinion in PCT/US2015/046845 dated Nov. 27, 2015.

(Continued)

*Primary Examiner* — Rebecca L Anderson
*Assistant Examiner* — Karen Cheng
(74) *Attorney, Agent, or Firm* — Neal, Gerber & Elsenberg LLP; Kevin A. O'Connor

(57) ABSTRACT

Pyridyl analogs of 1-(2-cyano-3,12-dioxooleana-1,9(11)-dien-28-oyl) imidazole and pharmaceutical compositions containing the same are provided.

19 Claims, 2 Drawing Sheets

(56) References Cited

OTHER PUBLICATIONS

International Preliminary Report on Patentability in PCT/US2015/046845 dated Mar. 9, 2017.
Yates et al. "Pharmacodynamics characterization of chemopreventive triterpenoids as exceptionally potent inducers of Nrf2-regulated genes" Mol. Cancer Ther. 2007 6(1):154-162.
Office Communication dated Jul. 17, 2017 in U.S. Appl. No. 15/505,327, filed Feb. 21, 2017.
Office Communication dated Oct. 30, 2017 in U.S. Appl. No. 15/505,327, filed Feb. 21, 2017.
Cao, Pharmacological Research, 2015, vol. 100, p. 135-147 and Supplementary Appendices (2015).

* cited by examiner

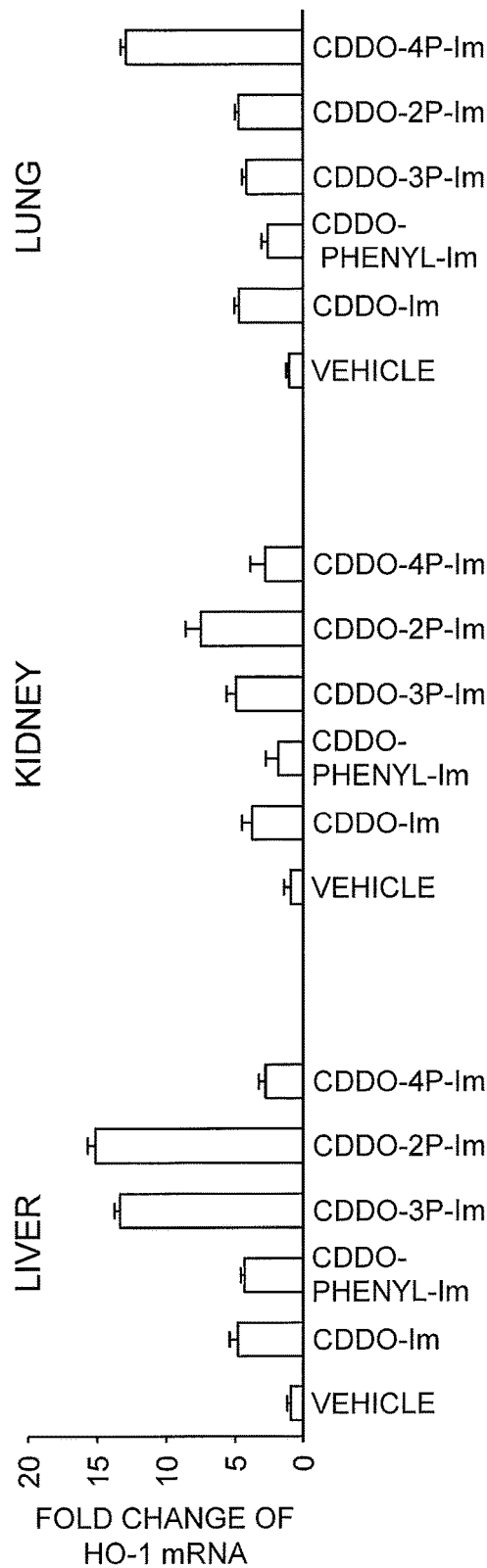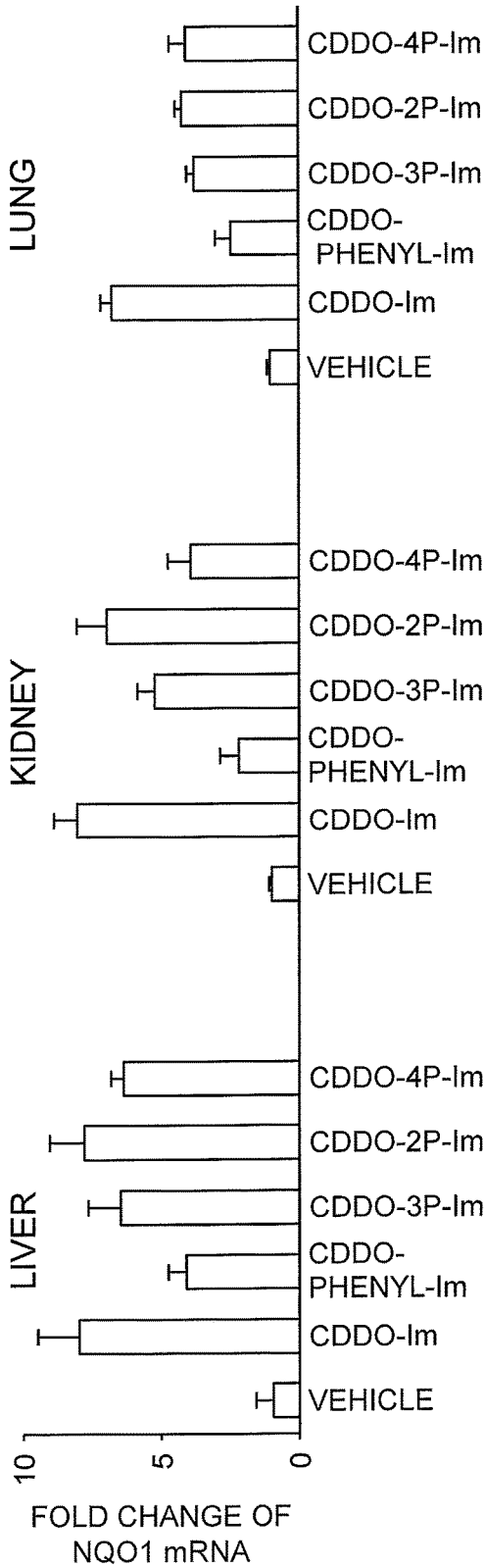

PYRIDYL ANALOGS OF 1-(2-CYANO-3,12-DIOXOOLEANA-1,9(11) DIEN-28-OYL) IMIDAZOLE

This application is a continuation-in-part of U.S. patent application Ser. No. 15/505,327, filed Feb. 21, 2017, which is a 371 application of PCT/US2015/046845 filed Aug. 26, 2015, which claims benefit of priority of Provisional Application No. 62/041,802 filed Aug. 26, 2014, the contents of which are incorporated herein by reference in their entirety.

BACKGROUND

One of the major needs in cancer prevention is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn & Roberts (1986) *J. Clin. Invest.* 78:329-332; Ohshima & Bartsch (1994) *Mutat. Res.* 305:253-264). The enzymes that mediate the constitutive synthesis of nitric oxide and prostaglandins from arginine and arachidonate, respectively, have relative little significance for either inflammation or carcinogenesis. In contrast, inducible nitric oxide synthase (iNOS) and inducible cycloxygenase (COX-2) both have critical roles in the response of tissues to injury or infectious agents (Moncada, et al. (1991) *Pharmacol. Rev.* 43:109-142; Nathan & Xie (1994) *Cell* 78:915-918; Siebert & Masferrer (1994) *Receptor* 4(1):17-23; Tamir & Tannebaum (1996) *Biochim. Biophys. Acta* 1288:F31-F36). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang, et al. (1994) *Cancer Res.* 54:701-708; Nishino, et al. (1988) *Cancer Res.* 48:5210-5215). However, the biological activity of these naturally occurring molecules is relatively weak, and therefore the synthesis of new analogs to enhance their potency has been undertaken (see, e.g., Honda, et al. (1997) *Bioorg. Med. Chem. Lett.* 7:1623-1628; Honda, et al. (1998) *Bioorg Med Chem Lett.* 8(19):2711-2714).

In this respect, U.S. Pat. No. 6,326,507, U.S. Pat. No. 6,552,075, U.S. Pat. No. 7,288,568, U.S. Pat. No. 7,863,327, U.S. Pat. No. 8,034,955, US 2009/0060873, US 2009/0048204, WO 2008/136838 and WO 2009/023232 teach the use of 2-cyano-3,12-dioxooleana-1,9(11)-dien-28-oic acid (CDDO), and derivatives thereof such as 2-cyano-3,12-dioxoolean-1,9(11)-dien-28-oic acid methyl ester (CDDO-Me) and amide derivatives, for the treatment of diseases such as cancer, Alzheimer's disease, Parkinson's disease, inflammatory bowel diseases, and multiple sclerosis. Similarly, U.S. Pat. No. 6,974,801 and WO 2004/064723 teach the use of 2-cyano-3,12-dioxooleana-1,9(11)-dien-28-onitrile (CNDDO), 1-(2-cyano-3,12-dioxooleana-1,9(11)-dien-28-oyl) imidazole (CDDO-Im), 1-(2-cyano-3,12-dioxooleana-1,9(11)-dien-28-oyl)-2-methylimidazole, and 1-(2-cyano-3,12-dioxooleana-1,9(11)-dien-28-oyl)-4-methylimidazole in the prevention or treatment of cancer, Alzheimer's disease, Parkinson's disease, multiple sclerosis, rheumatoid arthritis, and other inflammatory diseases. Furthermore, the use of triterpenoids such as CDDO, CDDO-Me, CDDO-Im, and CDDO-Ethylamide in stimulating the growth and repair of bone and cartilage (US 2008/0233195 and WO 2008/064132) as well as in inhibiting HIV-1 replication (WO 2005/046732) has been described. US 2009/0326063 further teaches the use of synthetic triterpenoids in the prevention and treatment of renal/kidney disease, insulin resistance/diabetes, fatty liver disease, and/or endothelial dysfunction/cardiovascular disease.

Combination therapies of CDDO or CDDO-Me and a chemotherapeutic agent, immunosuppressive agent, or proteasome inhibitor are described in U.S. Pat. No. 7,435,755, U.S. Pat. No. 7,795,305, US 2009/0018146, US 2009/0048205, WO 2002/047611 and WO 2009/023845 for the treatment of cancer and graft versus host disease. Moreover, formulations for improved oral bioavailability of CDDO-Me are disclosed in WO 2010/093944.

Given the activity of CDDO and CDDO-Me, additional oleanolic acid derivatives have been developed for use in treating cancer, cardiovascular disease, neurodegenerative disease, renal/kidney disease, diabetes, arthritis and inflammatory conditions such as obesity, hypertension, atherosclerosis, coronary heart disease, stroke, peripheral vascular disease, hypertension, nephropathy, neuropathy, myonecrosis, ulcerative colitis, Crohn's disease, irritable bowel syndrome, retinopathy and metabolic syndrome. See U.S. Pat. No. 7,915,402, U.S. Pat. No. 7,943,778, US 2010/0048887, US 2010/0048892, US 2010/0048911, US 2011/0245206 and US 2011/0245233.

SUMMARY OF THE INVENTION

The present invention is a triterpenoid compound of Formula I, or a hydrate, isomer, prodrug or pharmaceutically acceptable salt thereof:

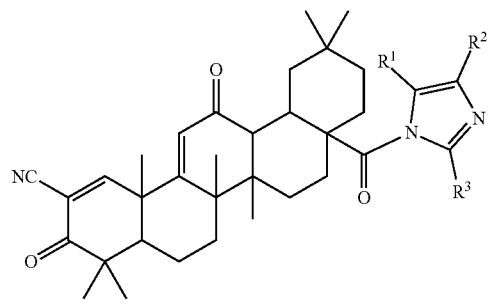

Formula I wherein one or more of $R^1$, $R^2$ or $R^3$ is independently a substituted or unsubstituted heteroaryl group, cycloalkyl group, heterocyclyl group, carboxamide group, nitrile group, haloalkyl group, or acyl group, and the remaining R groups are hydrogen. In a particular embodiment, the compound is provided in a pharmaceutical composition.

BRIEF DESCRIPTION OF THE DRAWINGS

FIG. 2A and FIG. 2B show the induction of cytoprotective enzyme expression in mouse liver, kidney and lung. CB57BL/6 mice were gavaged with 1 μmole of each triterpenoid. Six hours later, organs were harvested, RNA was extracted, and mRNA levels for HO-1 (FIG. 2A) and NQO1 (FIG. 2B) were quantified by real-time PCR analysis. Results are presented as the fold induction for each compound compared to the vehicle (DMSO) control. Data are presented as mean±SE of six mice per group.

DETAILED DESCRIPTION OF THE INVENTION

Figure 1:
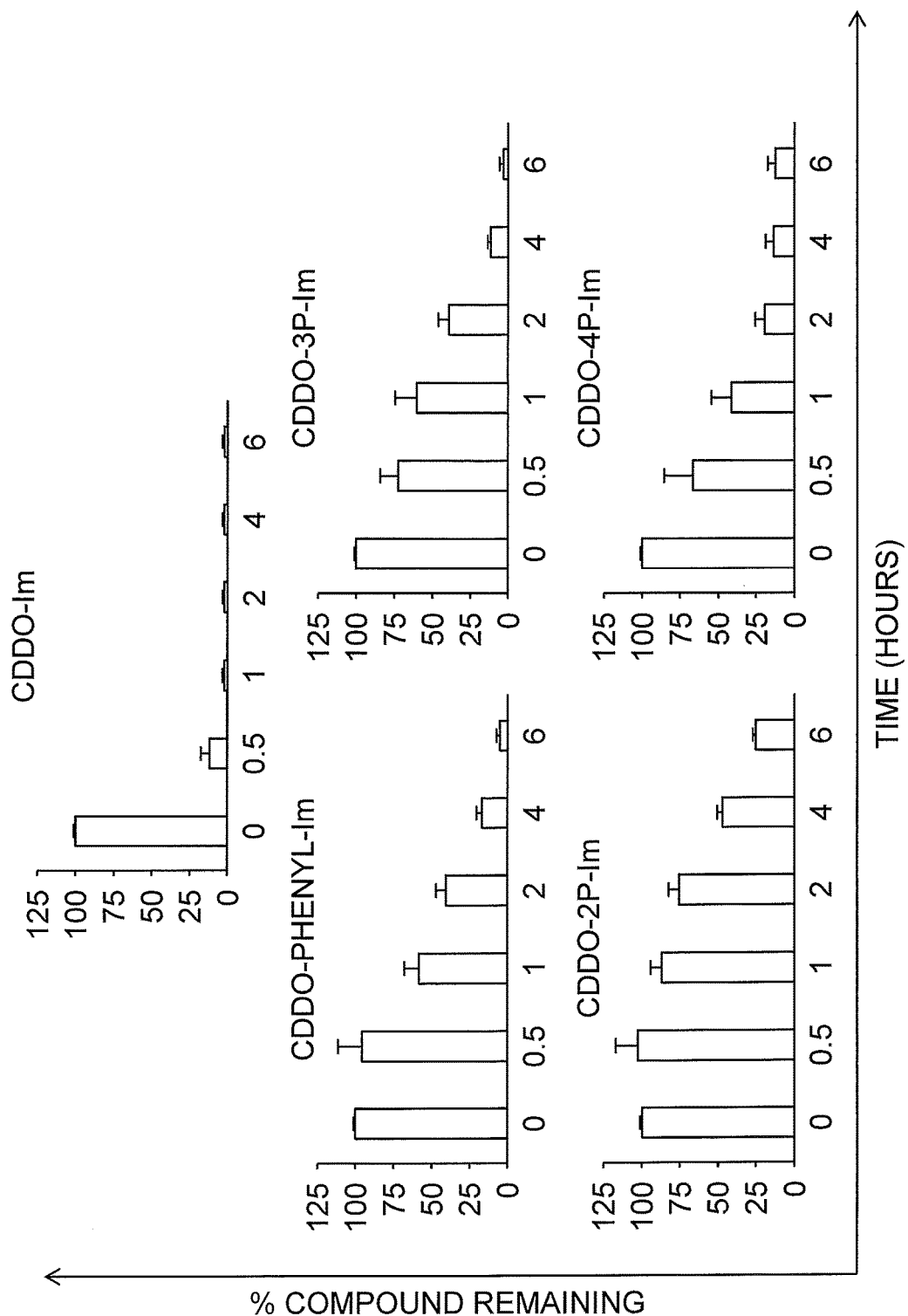
FIG. 1 shows the amount of compounds of the invention, which remained after a 6 hour incubation in human plasma at 37° C.

Pyridyl analogs of CDDO-Im 1 have now been developed, which are more stable in human plasma and achieve a higher concentration in target tissues such as liver, pancreas, kidney and lungs.

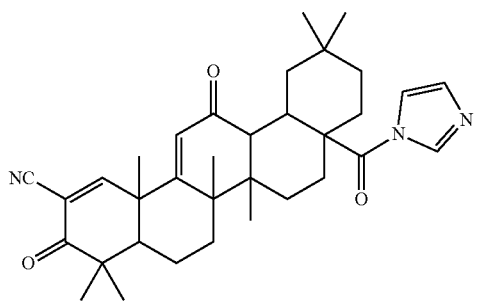

1

The compounds described herein are therefore of use in the treatment of disease, especially inflammatory diseases and cancer. Compounds particularly embraced by this invention have the structure of Formula I, which includes hydrates, isomers, prodrugs or pharmaceutically acceptable salts of Formula I:

Formula I

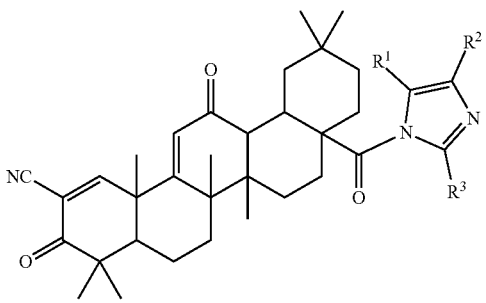

wherein one or more of $R^1$, $R^2$ or $R^3$ is independently a heteroaryl group, cycloalkyl group, heterocyclyl group, carboxamide group, nitrile group, haloalkyl group, or acyl group, each of which may be substituted or unsubstituted where appropriate, and the remaining R groups are hydrogen. In a particular embodiment, $R^2$ is a substituted or unsubstituted aryl group, heteroaryl group, cycloalkyl group or heterocyclyl group, and $R^1$ and $R^3$ are hydrogen.

The term "heteroaryl" refers to a five- or six-membered aromatic ring structure, wherein at least one of the aromatic ring atoms is nitrogen, oxygen or sulfur, and wherein the monovalent group is composed of carbon, hydrogen, aromatic nitrogen, aromatic oxygen or aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, and chromenyl, wherein the point of attachment is one of the aromatic atoms. In particular embodiments, the heteroaryl is a pyridyl group.

"Cycloalkyl" means a non-aromatic mono- or multicyclic ring system including about 3 to about 10 carbon atoms, preferably about 5 to about 10 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocyclyl" or "heterocycloalkyl" means a non-aromatic saturated monocyclic or multicyclic ring system including about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of suitable bicyclic heterocyclyl rings include decahydro-isoquinoline, decahydro-[2,6]naphthyridine, and the like.

As used herein, a "carboxamide" or "carboxamide group" refers to a —C(=O)NH$_2$ group.

The term "nitrile" or "nitrile group" is intended to refer to a —C≡N group.

As used herein, "alkyl" or "alkyl group" includes linear or branched saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include, but are not limited to, methyl, ethyl, n-propyl, isopropyl, n-butyl, isobutyl, sec-butyl, t-butyl, n-pentyl, sec-pentyl, 3-(2-methyl)butyl, 2-pentyl, 2-methylbutyl, n-hexyl, and 2-methylpentyl. In particular embodiments, an alkyl of this invention is a $C_{1-6}$ alkyl, $C_{1-5}$ alkyl, $C_{1-4}$ alkyl, alkyl, or $C_{1-2}$ alkyl.

The term "haloalkyl group" refers to a linear or branched alkyl group substituted by one or more halogen atoms, the same or different, optionally selected from fluorine, chlorine, bromine, and iodine. Examples of this group include fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl.

"Acyl," as used herein alone or as part of another group, refers to a —C(=O)R radical, where R is, e.g., an aryl, alkyl, alkenyl, alkynyl, or cycloalkyl group.

The term "aryl" refers to a monovalent group with an aromatic carbon atom as the point of attachment, said carbon atom forming part of a five- or six-membered aromatic ring structure wherein the ring atoms are all carbon, and wherein the monovalent group is composed of carbon and hydrogen. Non-limiting examples of aryl groups include phenyl, methylphenyl, (dimethyl)phenyl, ethylphenyl, propylphenyl, —C$_6$H$_4$CH (CH$_3$)$_2$, —C$_6$H$_4$CH (CH$_2$)$_2$, methylethylphenyl, vinylphenyl, naphthyl, and the monovalent group derived from biphenyl. In particular embodiments, the aryl is a phenyl group.

As used herein, "alkenyl" or "alkenyl group" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Examples of alkenyl include, but are not limited to, ethenyl, propenyls, such as prop-1-en-1-yl, prop-1-en-2-yl, prop-2-en-1-yl, prop-2en-2-yl, cycloprop-1-en-1-yl; cycloprop-2-en-1-yl; butenyls such as but-1-en-1-yl, but-1-en-2-yl, 2-methyl-prop-1-en-1yl, but-2-en-1-yl, but-2-en-1-yl, but-2-en-2-yl, buta-1,3-dien1-yl, beta-1,3-dien-2-yl, cyclobut-1-en-1-yl, cyclobut-1-en3-yl, cyclobuta-1,3-dien-1-yl.

As used herein, an "alkynyl" or "alkynyl group" refers to an unsaturated branched, straight-chain or cyclic monovalent hydrocarbon radical having at least one carbon-carbon triple bond derived by the removal of one hydrogen atom from a single carbon atom of a parent alkyne. Examples of alkynyl groups include, but are not limited to, ethynyl, propynyl, butynyls, propargyl, and the like.

Any of the groups described herein may be unsubstituted or optionally substituted. When modifying a particular group, "substituted" means that the group the term modifies may, but does not have to, be substituted. Substitutions include the replacement of an available hydrogen with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

Exemplary compounds within the scope of this invention include, but are not limited to:

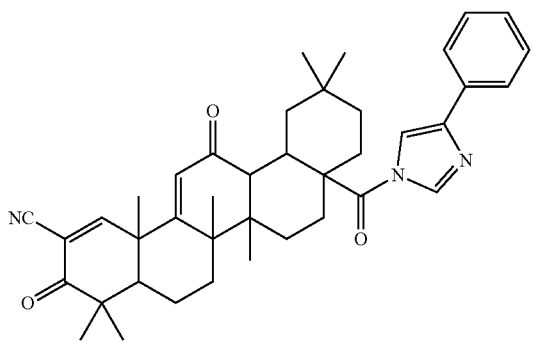

2

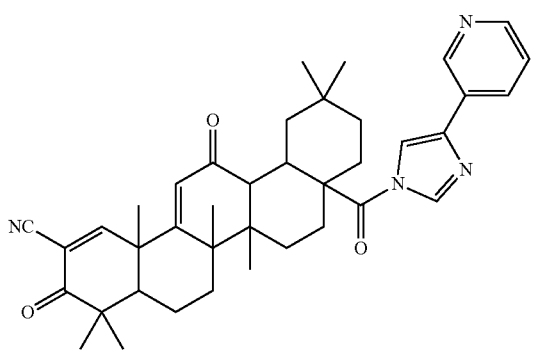

3

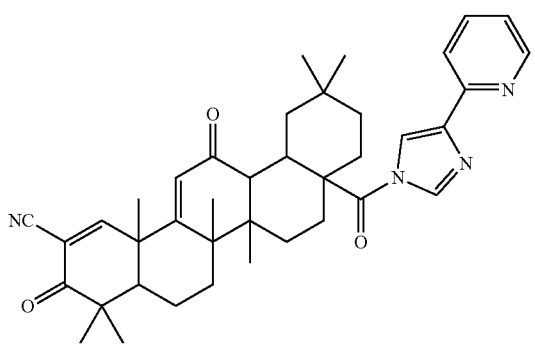

4

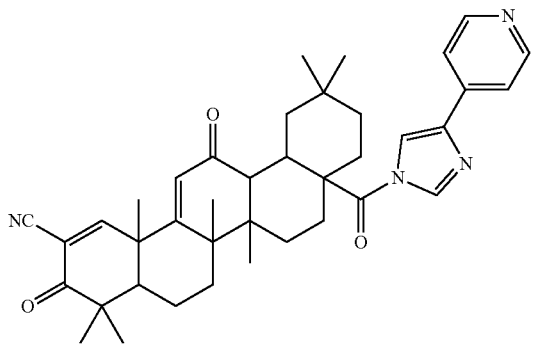

5

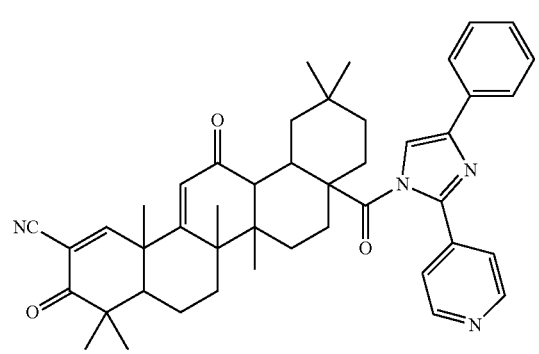
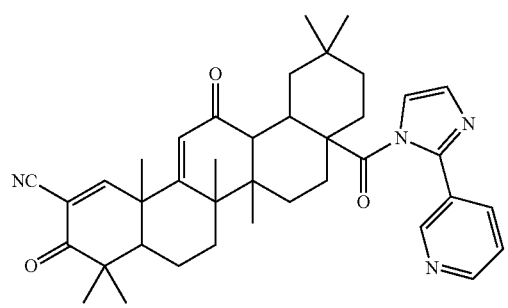

16
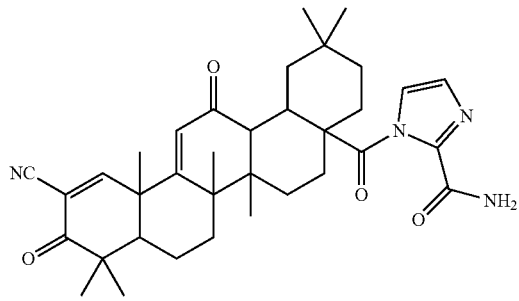

17
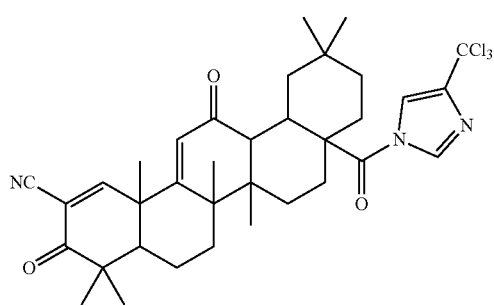

18
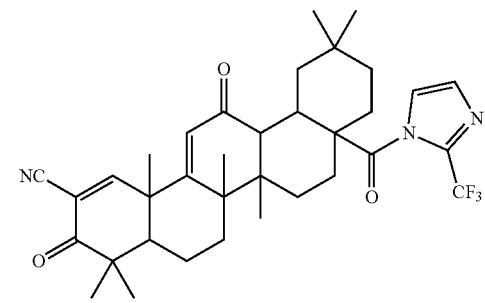

19
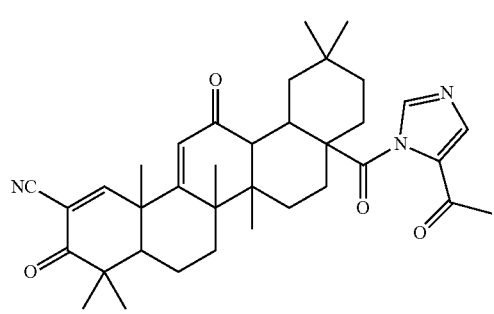

20
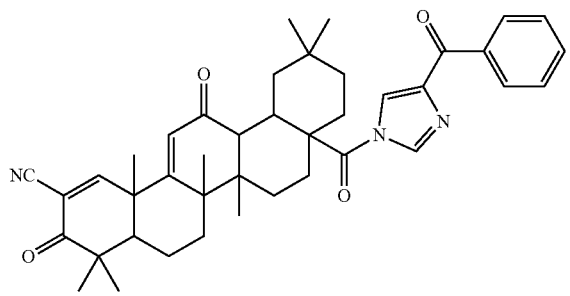

21
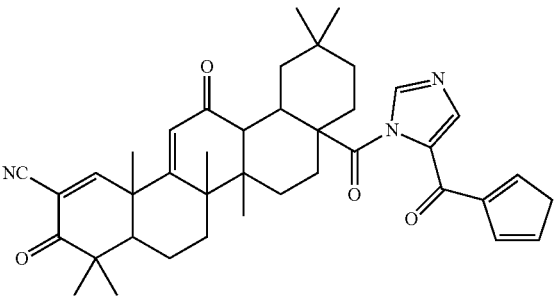

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

"Pharmaceutically acceptable salts" means salts of compounds of the present invention which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and di-carboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Compounds of the invention may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A compound of this invention may be administered in a pharmaceutical composition by various routes including, but not limited to, oral, subcutaneous, intravenous, or intraperitoneal administration (e.g. by injection). Depending on the route of administration, the active compound may be coated in a material to protect the compound from the action of acids and other natural conditions which may inactivate the compound.

For example, to administer the therapeutic compound by other than parenteral administration, it may be necessary to coat the compound with, or co-administer the compound with, a material to prevent its inactivation. By way of illustration, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan, et al. (1984) *J. Neuroimmunol.* 7:27).

The compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

One or more compounds of the invention are administered at a therapeutically effective dosage sufficient to treat a condition in a subject. A "therapeutically effective dosage" preferably reduces the amount of symptoms of the condition in the infected subject by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans.

The triterpenoid compounds of the invention are of use in modulating IFN-γ-induced NO production in macrophages, said composition having an $IC_{50}$ value of at least less than 0.6 μM, more preferably less than 0.020 μM.

In one embodiment, the instant compounds are of use in a method of modulating excessive nitric oxide or prostaglandin formation in a subject by administering to a subject a pharmaceutically effective amount of one or more triterpenoid compounds, such that the nitric oxide or prostaglandin formation is modulated.

In a further embodiment, the compounds of the invention are of use in a method of preventing or treating a disorder characterized by overexpression of iNOS or COX-2 genes, wherein the method includes administering to a subject a pharmaceutically effective amount of one or more triterpenoid compounds, such that the disorder is prevented or treated. In a preferred embodiment, the disorder includes cancer, diabetic nephropathy, neurodegenerative disease, rheumatoid arthritis, inflammatory bowel disease, and other diseases whose pathogenesis is believed to involve excessive production of either nitric oxide or prostaglandins. In a particular embodiment, the neurodegenerative disease includes Parkinson's disease, Alzheimer's disease, multiple sclerosis, and amyotrophic lateral sclerosis. The cancer may include, e.g., a leukemic cancer or a solid cancer. A leukemic cancer is a cancer of a blood cell, a myeloid cell, a monocytic cell, a myelocytic cell, a promyelocytic cell, a myeloblastic cell, a lymphocytic cell, or a lymphoblastic cell. A solid cancer is a cancer of a bladder cell, a breast cell, a lung cell, a colon cell, a prostate cell, a liver cell, a pancreatic cell, a stomach cell, a testicular cell, a brain cell, an ovarian cell, a skin cell, a brain cell, a bone cell, or a soft tissue cell.

Moreover, the invention provides methods for the treatment and prevention of graft versus host disease (GVHD) by providing a triterpenoid compound of the invention either alone or in conjunction with another agent, such as an immunosuppressive agent such as a corticosteroid or tacrolimus, or a chemotherapeutic agent for the treatment of GVHD. In graft versus host disease the donor immune system mounts a response against the host's organs or tissue. As CDDO compounds, either alone or in conjunction with other agents, can induce apoptosis by inhibiting Bcl-2 and have activity in lymphoid tissue, the instant compounds can also be used to provide therapy for graft versus host diseases.

The practice of the methods of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Genetics; Molecular Cloning A Laboratory Manual,* 2nd Ed. (Sambrook, et al., ed. (1989)) Cold Spring Harbor Laboratory Press; *Short Protocols in Molecular Biology,* 3rd Ed. (Ausubel, et al., ed. (1995)) Wiley, N.Y.; *DNA Cloning,* Volumes I and II (Glover, ed. (1985)); *Oligonucleotide Synthesis* (Gait, ed. (1984)); U.S. Pat. No. 4,683,195; *Nucleic Acid Hybridization* (Hames & Higgins, eds. (1984)); *Immunochemical Methods In Cell And Molecular Biology* (Mayer & Walker, eds. (1987)) Academic Press, London; *Handbook Of Experimental Immunology,* Volumes I-IV (Weir & Blackwell, eds. (1986)).

The invention is described in greater detail by the following non-limiting examples.

Example 1: Synthesis of Pyridine Analogs of CDDO-Im

The triterpenoids of the invention can be generally produced from natural compounds such as oleanolic acid, ursolic acid, betulinic acid, or hederagenin, or derivatives thereof that include additional A and/or C ring modifications. Synthesis of the compounds can be achieved using any conventional method of synthesizing similar triterpenoids such as CDDO or CDDO-Me. See, e.g., U.S. Pat. No. 6,326,507, U.S. Pat. No. 6,552,075, U.S. Pat. No. 6,974,801, U.S. Pat. Nos. 7,288,568, 7,863,327, U.S. Pat. No. 7,915,402, U.S. Pat. No. 7,943,778, U.S. Pat. No. 8,034,955, U.S. Pat. No. 8,071,632, U.S. Pat. No. 8,124,656, U.S. Pat. No. 8,124,799, U.S. Pat. No. 8,129,429 and WO 2009/146216.

The synthesis of CDDO imidazolides 2-5 was achieved by direct condensation of CDDO-Cl and the corresponding 4-substituted imidazolide pyridyls with a yield between 50-98% (Table 1). The imadozilides, 3-(1H-imidazol-4-yl) pyridine was obtained from a commercial source, while 4-(1H-imidazol-4-yl)pyridine and 2-(1H-imidazol-4-yl) pyridine were synthesized by known procedures (Horne, et al. (1994) *Heterocycles* 39:139-53; US 2010/026796).

TABLE 1

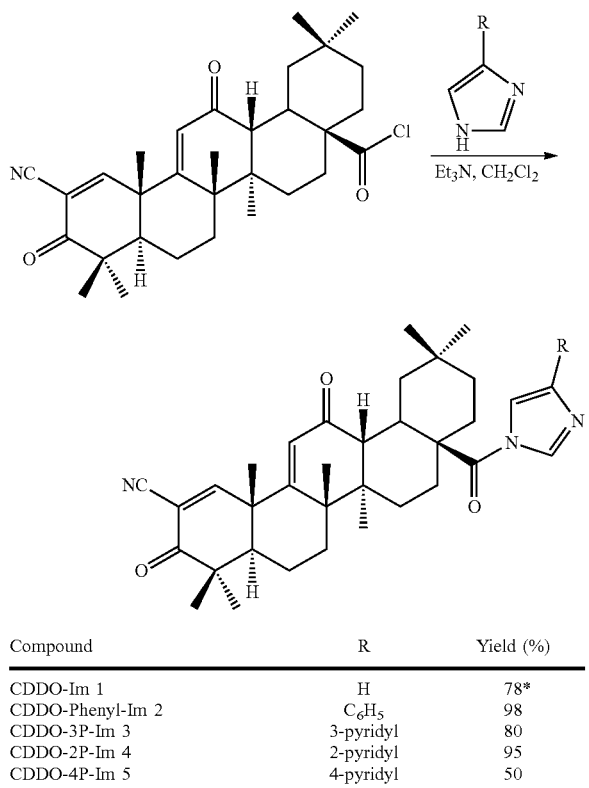

| Compound | R | Yield (%) |
|---|---|---|
| CDDO-Im 1 | H | 78* |
| CDDO-Phenyl-Im 2 | $C_6H_5$ | 98 |
| CDDO-3P-Im 3 | 3-pyridyl | 80 |
| CDDO-2P-Im 4 | 2-pyridyl | 95 |
| CDDO-4P-Im 5 | 4-pyridyl | 50 |

*Liby, et al. (2006) *Clin. Cancer Res.* 12: 4288-4293.

CDDO-Phenyl-Im 2 presents in its structure the phenyl-tethered imidazolide while the three other analogues incorporate a pyridyl group in the imidazolide in which the nitrogen position is variable. CDDO-3P-Im 3 possesses the nitrogen in meta (3 position), CDDO-2P-Im 4 in ortho (2 position) and CDDO-4P-Im 5 in para (4 position). The structures and the purity of the new triterpenoids were confirmed by NMR spectral analyses.

Example 2: Pyridine Analogs Induce Monocytic Differentiation

CDDO-Im 1 is a potent inducer of differentiation in U937 cells (Place, et al. (2003) *Clin. Cancer Res.* 9:2798-2806). Therefore, the activity of the CDDO-Im analogs was evaluated using the U937 leukemia cell line. CD11b (also known as Mac-1α or CR3 complement receptor) was used as a surface marker of monocytic differentiation, and its expression was measured by flow cytometry after 4 days of treatment with CDDO-Phenyl-Im 2, CDDO-3P-Im 3, CDDO-2P-Im 4, CDDO-4P-Im 5, CDDO-Im 1 (as positive control) or vehicle (DMSO). This analysis indicated that 30 nM CDDO-3P-Im was as effective as 30 nM CDDO-Im to induce differentiation of U937 cells (approximately a 3-fold induction of CD11b expression compared to the DMSO-treated cells), whereas CDDO-Phenyl-Im, CDDO-2P-Im, and CDDO-4P-Im were less active at this concentration. However, increasing the concentration to 100 nM enhanced the activity of CDDO-2P-Im and CDDO-4P-Im. Indeed, the highest level of differentiation was obtained using 100 nM of CDDO-2P-Im (approximately a 4-fold induction of CD11b).

As CDDO-Im and CDDO-3P-Im at 100 nM induced cell death in the differentiation assay, U937 cells were treated for 48 hours to measure apoptosis. Both CDDO-Im and CDDO-3P-Im increased annexin V staining, a marker of early apoptosis.

Example 3: Pyridine Analogs Inhibit NO Production

Because oxidative and inflammatory stress contribute to carcinogenesis (Albini & Sporn (2007) *Nature Rev. Cancer* 7:139-147), it was determined whether the pyridine analogues could block de novo synthesis of inducible nitric oxide synthase (iNOS), a critical enzyme involved in the inflammatory response (Kroncke, et al. (1998) *Clin. Exp. Immunol.* 113:147-156; Zamora, et al. (2000) *Mol. Med.* 6:347-373). Nitric oxide release was determined in RA W264.7 macrophage-like cells, after stimulation with 10 ng/ml interferon-γ (IFNγ) and a 24 hour-exposure to each compound at 0.625, 1.3, 2.5, 5, 10 and 20 nM. NO release was measured by Griess reaction and compared to CDDO-Im, which is a potent suppressor of iNOS (Place, et al. (2003) *Clin. Cancer Res.* 19:2798-2806). This analysis indicated that the new analogues were slightly less potent than CDDO-Im for blocking NO production. However, each analog inhibited NO production in the low nanomolar range with $IC_{50}$ values between 2-15 nM (Table 2). The order of potency in the NO assay was similar to the results obtained in the U937 differentiation assay with CDDO-Im (2.0 nM) and CDDO-3P-Im (4.3 nM) being the most active and CDDO-Phenyl-Im being the least active (14.7 nM).

TABLE 2

| Compound | $IC_{50}$ (nM) Mean ± SE |
| --- | --- |
| CDDO-Im 1 | 2.0 ± 0.6 |
| CDDO-Phenyl-Im 2 | 14.7 ± 2.9 |

TABLE 2-continued

| Compound | $IC_{50}$ (nM) Mean ± SE |
| --- | --- |
| CDDO-3P-Im 3 | 4.3 ± 0.7 |
| CDDO-2P-Im 4 | 5.8 ± 1.1 |
| CDDO-4P-Im 5 | 9.0 ± 0.6 |

Example 4: Stability of Pyridine Analogs in Human Serum

Since CDDO-Im is not stable in human plasma, the stability of the CDDO-Im analogs was determined. Compounds were incubated in human plasma at 37° C. for up to 6 hours. The compounds were extracted with acetonitrile at six different time points (0, 0.5, 1, 2, 4 and 6 hours), centrifuged, and the percent of starting material remaining in the supernatant was measured by liquid chromatography-mass spectrometry (LC-MS). This analysis indicated that CDDO-Im was rapidly metabolized; more than 88% of the CDDO-Im was lost within 30 minutes, and this loss increased to 98% within the next 5 hours (FIG. 1). In contrast, the degradation graphs of the CDDO-Im analogs revealed greater stability compared to CDDO-Im (FIG. 1). For the least stable compound, CDDO-4P-Im, 42% of the starting material was still detected after a 1-hour incubation, while more than 85% of CDDO-2P-Im remained in plasma. The concentrations then decreased gradually over 6 hours. CDDO-2P-Im was the most stable analog with more than 50% left in plasma after 4 hours. CDDO-Phenyl-Im, CDDO-3P-Im, and CDDO-4P-Im were all more stable than CDDO-Im. Further LC-MS analysis on the samples revealed that CDDO-Im was essentially converted to its parent molecule 2-cyano-3,12-dioxooleana-1,9 (11)-dien-28-oic acid (CDDO), whose concentration increased over time in human plasma. Unexpectedly, the CDDO-Im analogs are metabolized differently from CCDO-Im, as no traces of CDDO were detected with any of the other compounds at any time point. Instead, an oxidized derivative was detected on the chromatogram, in the form of an adduct on the molecule of +16 in MW (N-oxide).

Example 5: Tissue Distribution CDDO-Im Pyridine Analogs

To determine concentrations of the CDDO-Im analogs in various organs, an in vivo evaluation was conducted in C57BL/6 mice. Six hours after a single gavage with 1 µmole of compound, the mice were sacrificed and the tissues were collected. Table 3 shows concentrations measured in the liver, pancreas, kidney, lung, whole blood and plasma of mice by LC-MS.

TABLE 3

| | Compound Concentration (µmole/kg) Mean ± SE | | | | |
| --- | --- | --- | --- | --- | --- |
| Tissue | 1 | 2 | 3 | 4 | 5 |
| Liver | 1.7 ± 0.32 | 12.2 ± 1.27 | 5.9 ± 0.57 | 14.9 ± 2.58 | 2.8 ± 0.47 |
| Pancreas | 0.31 ± 0.09 | 1.97 ± 0.19 | 2.52 ± 0.24 | 3.55 ± 0.39 | 0.30 ± 0.04 |
| Kidney | 0.24 ± 0.08 | 5.79 ± 0.25 | 1.47 ± 0.24 | 3.70 ± 0.55 | 0.35 ± 0.06 |
| Lungs | 0.19 ± 0.05 | 1.28 ± 0.17 | 2.49 ± 0.44 | 2.63 ± 0.41 | 0.17 ± 0.05 |
| Whole Blood | 0.03 ± 0.01 | 0.35 ± 0.03 | 0.16 ± 0.02 | 0.53 ± 0.02 | 0.04 ± 0.1 |
| Plasma | 0.06 ± 0.02 | 0.12 ± 0.01 | 0.15 ± 0.04 | 0.52 ± 0.02 | 0.03 ± 0.01 |

The bioavailability of CDDO-3P-Im 3, CDDO-2P-Im 4 and CDDO-Phenyl-Im 2 was better than for CDDO-Im 1 as demonstrated by the higher drug concentrations attained in each organ. In contrast, levels obtained with CDDO-4P-Im 5 were similar to CDDO-Im 1. The highest levels for all of these compounds were detected in the liver with concentrations of 12-15 µM for CDDO-2P-Im 4 and CDDO-Phenyl-Im 2 vs. 1.7 µM for CDDO-Im 1. In kidneys, the highest concentration was obtained with CDDO-Phenyl-Im 2 (5.8 µM), followed by CDDO-2P-Im 4, CDDO-3P-Im 3, and CDDO-4P-Im 5. Very low concentrations of CDDO-Im 1 (approximately 0.3 µM) were detected in the pancreas, with much higher levels obtained with CDDO-2P-Im 4 (3.5 µM), CDDO-3P-Im 3 (2.5 µM), and CDDO-Phenyl-Im 2 (2 µM). Lower tissue levels were found in lungs for all of the compounds compared to the liver and kidney, but drug levels in the lungs were greater than 2.5 µM for CDDO-3P-Im 3 and CDDO-2P-Im 4 vs. 0.2 µM for the parental CDDO-Im 1. The concentration of triterpenoids was higher in whole blood than in plasma. While the detection of transformation products was also carried out in plasma, no traces of any oxidized forms could be found, suggesting a distinct metabolization in mice vs. humans.

Example 6: CDDO-Im Pyridine Analogs Induce HO-1 and NQO1 Expression In Vivo

Synthetic triterpenoids such as CDDO-Im strongly activate the Nrf2/ARE pathway; Nrf2 is a transcription factor that regulates numerous cytoprotective and anti-inflammatory genes (Liby, et al. (2005) *Cancer Res.* 65:4789-98; Yates, et al. (2007) *Mol. Cancer Therapeut.* 6:154-62). Therefore, the ability of the new pyridine compounds to induce transcription of the Nrf2 target genes HO-1 and NQO1 in vivo was assessed. In tissues harvested from mice six hours after gavage with the drugs, an increase in the expression of HO-1 was observed with all triterpenoids, compared to the vehicle control (FIG. 2A). In the liver, CDDO-3P-Im and CDDO-2P-Im induced high levels of HO-1, which were about 3 times more elevated than with CDDO-Im (13.4- and 15.2-fold, respectively vs. 4.9-fold for CDDO-Im). CDDO-Phenyl-Im and CDDO-4P-Im presented similar induction of HO-1 compared to the parent molecule. While induction levels were lower in the kidney than in the liver, the overall profile in the kidney was similar, except that CDDO-Phenyl-Im was markedly less potent. The results obtained in lungs were, on the other hand, unexpected. Although CDDO-4P-Im did not accumulate in lungs based on the pharmacokinetic study summarized in Table 3, it notably induced gene expression in the lungs. HO-1 transcript levels were increased almost 3 times more than with CDDO-Im or any of the other compounds, while it was less potent than CDDO-Im in the liver and kidney.

Because HO-1 is regulated by transcription factors in addition to Nrf2 (Alam, et al. (1999) *J. Biol. Chem.* 274: 26071-8; Kensler, et al. (2007) *Ann. Rev. Pharmacol. Toxicol.* 47:89-116), induction of the prototypical Nrf2 target gene NQO1 was also examined. All of the CDDO-Im analogs induced the expression of NQO1 mRNA (FIG. 2B), although they were slightly less potent than CDDO-Im in the liver, with the exception of CDDO-Phenyl-Im which was markedly less potent than CDDO-Im. The same trend of NQO1 mRNA induction was observed both in liver and kidney, with CDDO-Im as the most potent compound, followed by CDDO-2P-Im, CDDO-3P-Im, CDDO-4P-Im and then CDDO-Phenyl-Im. In lungs, the pyridine analogs were less active than CDDO-Im but all displayed a 2.4- to 4-fold increase of NQO1 mRNA.

To confirm those findings, immunoblot analysis was performed for HO-1. Protein extracts were prepared from the homogenized mouse livers, kidneys and lung, and subsequently examined by western blot. This analysis indicated that HO-1 protein levels were increased in parallel with mRNA transcript levels.

What is claimed is:

1. A triterpenoid compound having the structure of Formula I, or a hydrate, stereoisomer, prodrug or pharmaceutically acceptable salt thereof:

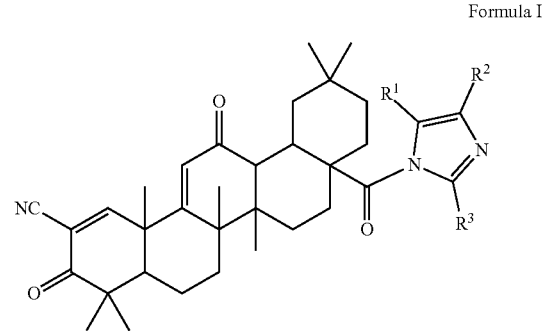

Formula I wherein one or more of $R^1$, $R^2$ or $R^3$ is independently a substituted or unsubstituted carboxamide group and the remaining R groups are hydrogen.

2. A pharmaceutical composition comprising the compound of claim 1 or a hydrate, stereoisomer, or pharmaceutically acceptable salt thereof in admixture with a pharmaceutically acceptable carrier.

3. The triterpenoid compound of claim 1 or a hydrate, stereoisomer, or pharmaceutically acceptable salt thereof, wherein $R^1$ is a substituted or unsubstituted carboxamide and $R^2$ and $R^3$ are hydrogen.

4. The triterpenoid compound of claim 1 or a hydrate, stereoisomer, or pharmaceutically acceptable salt thereof, wherein $R^2$ is a substituted or unsubstituted carboxamide and $R^1$ and $R^3$ are hydrogen.

5. The triterpenoid compound of claim 1 or a hydrate, stereoisomer, or pharmaceutically acceptable salt thereof, wherein $R^3$ is a substituted or unsubstituted carboxamide and $R^1$ and $R^2$ are hydrogen.

6. The triterpenoid compound of claim 1 or a hydrate, stereoisomer, or pharmaceutically acceptable salt thereof, wherein the compound is

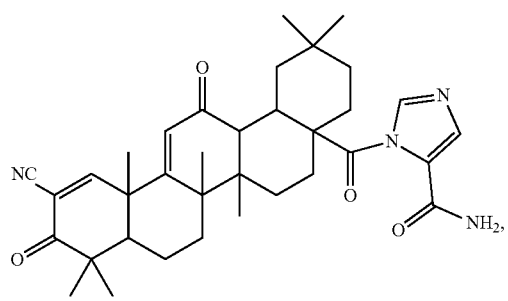

7. A method of treating disorder characterized by overexpression of iNOS or COX-2 genes, the method comprising administering to a subject in need thereof a pharmaceutically effective amount of the triterpenoid compound of claim 1 or a hydrate, stereoisomer, or pharmaceutically acceptable salt thereof.

8. The method of claim 7, wherein the disorder is cancer.

9. A triterpenoid compound having the structure of Formula I, or a hydrate, stereoisomer, prodrug or pharmaceutically acceptable salt thereof:

Formula I wherein one or more of $R^1$ or $R^3$ is independently a substituted or unsubstituted nitrile group, haloalkyl group, or acyl group, and the remaining R groups are hydrogen.

10. The triterpenoid compound of claim 9 or a hydrate, stereoisomer, or pharmaceutically acceptable salt thereof, wherein $R^1$ is a substituted or unsubstituted nitrile and $R^2$ and $R^3$ are hydrogen.

11. The triterpenoid compound of claim 9 or a hydrate, stereoisomer, or pharmaceutically acceptable salt thereof, wherein $R^3$ is a substituted or unsubstituted nitrile and $R^1$ and $R^2$ are hydrogen.

12. The triterpenoid compound of claim 9 or a hydrate, stereoisomer, or pharmaceutically acceptable salt thereof, wherein $R^1$ is a substituted or unsubstituted haloalkyl and $R^2$ and $R^3$ are hydrogen.

13. The triterpenoid compound of claim 9 or a hydrate, stereoisomer, or pharmaceutically acceptable salt thereof, wherein $R^3$ is a substituted or unsubstituted haloalkyl and $R^1$ and $R^2$ are hydrogen.

14. The triterpenoid compound of claim 9 or a hydrate, stereoisomer, or pharmaceutically acceptable salt thereof, wherein $R^1$ is a substituted or unsubstituted acyl and $R^2$ and $R^3$ are hydrogen.

15. The triterpenoid compound of claim 9 or a hydrate, stereoisomer, or pharmaceutically acceptable salt thereof, wherein $R^3$ is a substituted or unsubstituted acyl and $R^1$ and $R^2$ are hydrogen.

16. A pharmaceutical composition comprising the compound of claim 9 or a hydrate, stereoisomer, or pharmaceutically acceptable salt thereof in admixture with a pharmaceutically acceptable carrier.

17. A method of treating disorder characterized by overexpression of iNOS or COX-2 genes, the method comprising administering to a subject in need thereof a pharmaceutically effective amount of the triterpenoid compound of claim 9 or a hydrate, stereoisomer, or pharmaceutically acceptable salt thereof.

18. The method of claim 17, wherein the disorder is cancer.

19. A triterpenoid compound or a hydrate, stereoisomer, or pharmaceutically acceptable salt thereof, wherein the compound is selected from the group consisting of:

-continued
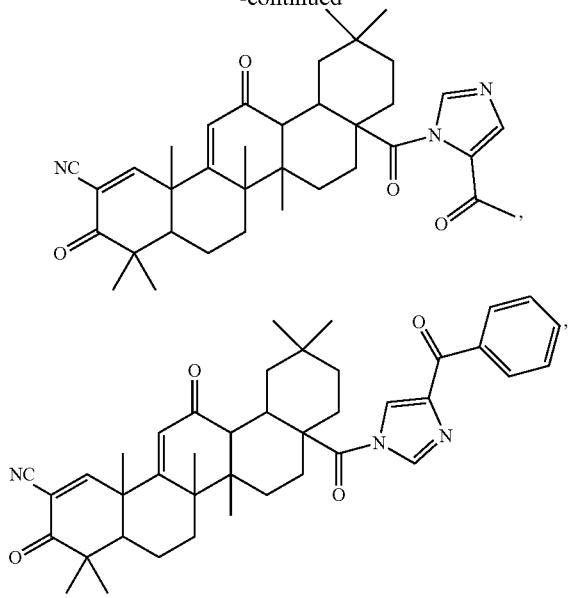
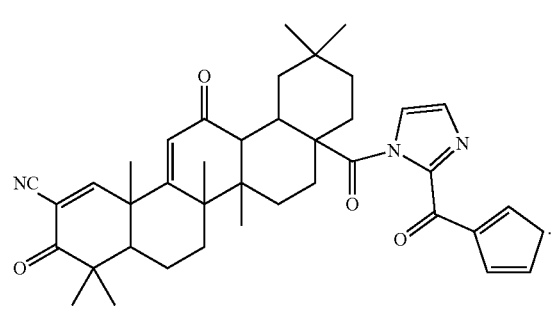
* * * * *